United States Patent
Bouvier

(10) Patent No.: US 8,849,370 B2
(45) Date of Patent: Sep. 30, 2014

(54) MOVABLE IMAGING SYSTEM COMPRISING AN INTEGRATED DISPLAY

(75) Inventor: Bernard Bouvier, Eragny sur Oise (FR)

(73) Assignee: General Electric Company, Schenectady, NY (US)

( * ) Notice: Subject to any disclaimer, the term of this patent is extended or adjusted under 35 U.S.C. 154(b) by 55 days.

(21) Appl. No.: 13/184,195

(22) Filed: Jul. 15, 2011

(65) Prior Publication Data

US 2012/0016222 A1 Jan. 19, 2012

(30) Foreign Application Priority Data

Jul. 15, 2010 (FR) ...................................... 10 55751

(51) Int. Cl.
*A61B 5/05* (2006.01)
*A61B 6/10* (2006.01)
*A61B 6/00* (2006.01)

(52) U.S. Cl.
CPC .................. *A61B 6/462* (2013.01); *A61B 6/102* (2013.01); *A61B 6/4441* (2013.01)
USPC ............ 600/407; 600/409; 600/410; 600/437

(58) Field of Classification Search
USPC ................................................ 600/407–469
See application file for complete search history.

(56) References Cited

U.S. PATENT DOCUMENTS

| | | | |
|---|---|---|---|
| 4,852,500 A * | 8/1989 | Ryburg et al. ................. | 108/105 |
| 5,924,988 A * | 7/1999 | Burris et al. ................... | 600/437 |
| 6,597,294 B1 * | 7/2003 | Ariens ..................... | 340/995.26 |
| 8,023,262 B2 * | 9/2011 | Ligtenberg et al. ...... | 361/679.55 |
| 8,242,906 B2 * | 8/2012 | Fawcett ...................... | 340/568.2 |
| 2003/0233040 A1 * | 12/2003 | Sakaniwa ..................... | 600/407 |
| 2004/0081285 A1 | 4/2004 | Gotoh | |
| 2008/0132786 A1 * | 6/2008 | Asai et al. ..................... | 600/437 |
| 2008/0258929 A1 | 10/2008 | Maschke | |

FOREIGN PATENT DOCUMENTS

| | | |
|---|---|---|
| DE | 4423360 A1 | 1/1996 |
| DE | 102007052650 A1 | 5/2009 |
| WO | 2005074806 A1 | 8/2005 |

OTHER PUBLICATIONS

European Search Report from corresponding Application No. EP11173165, dated Sep. 26, 2011.

* cited by examiner

*Primary Examiner* — Sanjay Cattungal
(74) *Attorney, Agent, or Firm* — Global Patent Operation; Marc A. Vivenzio

(57) ABSTRACT

A medical imaging system is provided. The medical imaging system comprises a movable acquisition device, a processing unit and a display, wherein the display is fixed to the movable acquisition device.

8 Claims, 2 Drawing Sheets

MOVABLE IMAGING SYSTEM COMPRISING AN INTEGRATED DISPLAY

BACKGROUND OF THE INVENTION

1. Field of the Invention

Embodiments of the presenting invention generally relate to the area of interventional radiology.

2. Description of Related Art

The principle of interventional radiology procedures, for a user, consists of performing a surgical procedure on a patient with the assistance of a medical imaging system.

This medical imaging system allows the acquisition, processing and display of data in real time, such as the position of an instrument, for example, and/or a depiction of the inside of the patient.

An interventional radiology room conventionally comprises an imaging system secured to the floor. The imaging system conventionally comprises a device for acquiring intraoperative X-ray data; a remote processing unit which allows for the processing of the acquired data to convert the same into displayable images and/or for their merging with pre-operative images; and a fixed display (for example hanging from the ceiling of the interventional radiology room) enabling the display of images derived from the processing unit.

Interventional radiology has become indispensable for the therapeutic management of numerous pathologies.

This explains why the trend in hospital services is to invest in so-called hybrid intervention rooms. These hybrid intervention rooms allow the conducting of conventional interventional radiology as well as surgical operations usually performed in operating rooms. So that they can be used for interventions of different types, these hybrid rooms can be equipped with two tables, for example, a conventional interventional radiology table and a surgery table.

An imaging system was proposed by Siemens® in which the X-ray acquisition device is arranged at the end of a swivel arm able to be moved over the entire radiology room. The display consists of a monitor fixed to a wall of the room or several monitors fixed to a suspension mounted on rails on the ceiling. With this device, it is possible, in one room, to conduct two surgical procedures of different types using a single imaging system which can be moved from one operating table to another.

However, owing to the size of the acquisition device and of the swivel arm of said device, it is very difficult to position the display so that they can be seen by the user, irrespective of position.

BRIEF SUMMARY OF THE INVENTION

One purpose of the embodiments of the present invention is to provide an ergonomic imaging system allowing a display to be maintained in the field of vision of the user, irrespective of the position of the acquisition device.

More generally, one purpose of the embodiments of the present invention is to provide a medical imaging system that limits the risk that the display is hidden behind medical equipment in the interventional radiology room.

For this purpose, the embodiments of the invention provide a medical imaging system comprising a movable acquisition device, a processing unit and a display, wherein the display is fixed to the acquisition device and can be moved relative to the acquisition device.

Providing a display on an acquisition device which is movable ensures a clear view of the display by the user, irrespective of the position of the acquisition means in the interventional radiology room.

BRIEF DESCRIPTION OF THE SEVERAL VIEWS OF THE DRAWINGS

Other characteristics and advantages of the embodiments of the invention will become further apparent from the following description, which is solely illustrative and is non-limiting, with reference to the appended drawings in which.

DETAILED DESCRIPTION OF THE INVENTION

The medical imaging system according to the embodiments of the invention will now be described in more detail.

The medical imaging system allows the acquisition of a patient's X-ray data, the processing of this data in order to generate images, and the display of these images on a display.

Figure 1:
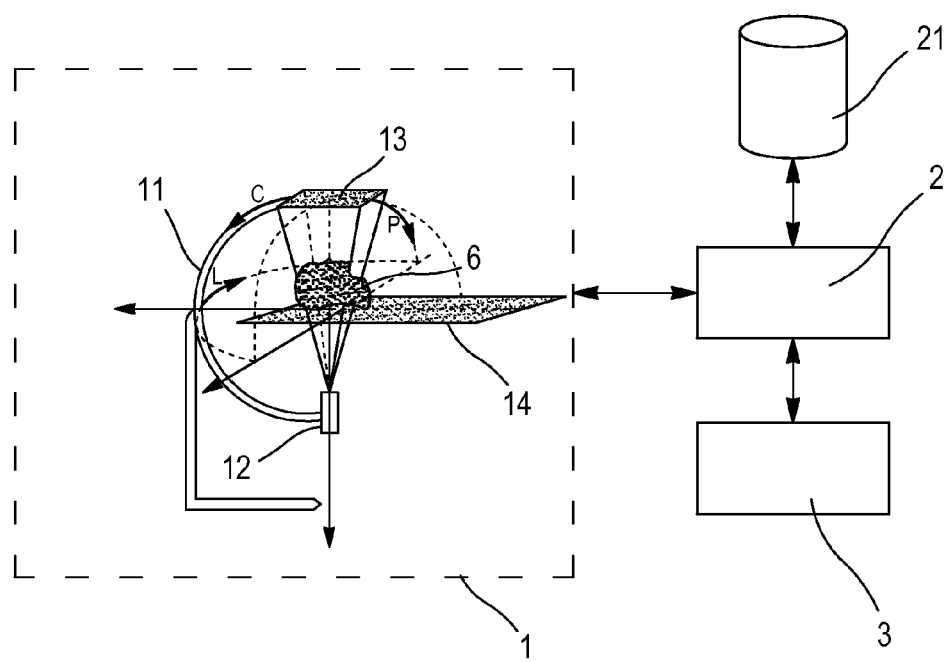
FIG. 1 illustrates an embodiment of the imaging system according to the invention.

With reference to FIG. 1, one embodiment of the imaging system is illustrated. The imaging system comprises an image acquisition device 1, an image processing unit 2 and an image display 3. The acquisition device 1 allows X-ray data to be obtained of a region in the patient 6 during an operation. The acquisition device 1 can be moved around the operation room. In particular, this allows two surgical procedures to be carried out assisted by a single imaging system, the procedures being performed on two tables located in the same operating room. The acquisition device 1 comprises a C-arm 11 which carries a radiation source 12 at one of its ends, and at its other end a sensor 13. The arm 11 is pivot mounted on a stand 15 that is column-shaped. As is conventional, the C-arm 11 is capable of being pivoted about the axis of a table 14 intended to receive the patient 6 to be imaged, and to be moved relative to this table 14 along various directions so as to allow adjustment of the positioning of said arm 11 relative to that part of the patient 6 it is desired to image. Once the C-arm is in position, the source 12 projects a conical radiation which is received by the sensor 13 after passing through the patient 6 to be imaged. The data acquired by the sensor 13 is transferred to the processing unit 2.

The processing unit 2 receives and processes the data derived from the acquisition device. The processing unit 2 is able to implement different imaging methods in relation to the type of interventional procedure to be carried out. For example, the processing unit 2 is capable of determining the current position of a medical instrument, and/or of merging two-dimensional intraoperative images with pre-operative images, such as a three-dimensional model of the patient's vascular system. The processing unit 2 can be integrated in the acquisition device 1, or can be separate from the acquisition device 1. The processing unit 2 is, for example, one or more computers, one or more processors, or one or more microcontrollers, one or more micro-computers, one or more programmable logic controllers, one or more application-specific integrated circuits, or other programmable circuits or other devices which include a computer such as a work station. The processing unit 2 is coupled with one or more memories 21 which can be integrated in or separate from the processing unit 2. The memory 21 may be a ROM/RAM memory of the processing unit 2, a CD-ROM, a USB key, or a memory of a central server. Once the images have been processed by the processing unit 2, they are displayed on the display 3.

The display 3 allows display of the image or images derived from the processing unit 2 and of the patient's biological data such as heart rate, etc. The display is coupled with the processing unit via connection cables. The display 3 is, for example, one or more monitors, one or more LCD screens, one or more flat screens, one or more plasma screens, or a combination thereof, or any type of display device known to persons skilled in the art.

The display 3 may be integrated in the acquisition device 1. In one embodiment, the display 3 is secured to the acquisition device 1 via an articulated supporting structure 31, 32, 33, 34. This articulated supporting structure 31, 32, 33, 34 allows the display 3 to travel between a retracted position illustrated in FIG. 2 and a deployed position illustrated FIG. 3. The supporting structure may comprise a telescopic arm. The use of a telescopic arm allows limitation of the volume taken up by the supporting structure when the display 3 is in a retracted position. In the embodiment illustrated in FIGS. 2 and 3, the supporting structure comprises two telescopic arms 31, 32. This facilitates adjustment of the position of the display 3 to achieve optimal reading comfort for the user.

The first telescopic arm 31 is fixed to the stand 15 of the acquisition device 1 via a first connection 33 having at least two degrees of freedom. The free end of the first telescopic arm 31 is connected to the second telescopic arm 32 via a second connection 34 having at least two degrees of freedom. The free end of the second telescopic arm 32 can be connected to the display 3 via a third connection having at least one degree of freedom. The use of connections 33, 34 having at least two degrees of freedom can facilitate the orientation and positioning of the display 3 by the user. The different connections 33, 34 of the system can be ball-joints with three degrees of freedom. Each telescopic arm 31, 32 may comprise a cut-out to pass connection cables. This allows an improvement in the ergonomics of the imaging system. The connection cables can be of different types. For example, in one embodiment, the connection cables are helical cables. This can impart sufficient flexibility to the connection cables while limiting the space taken up by the imaging system.

Figure 2:
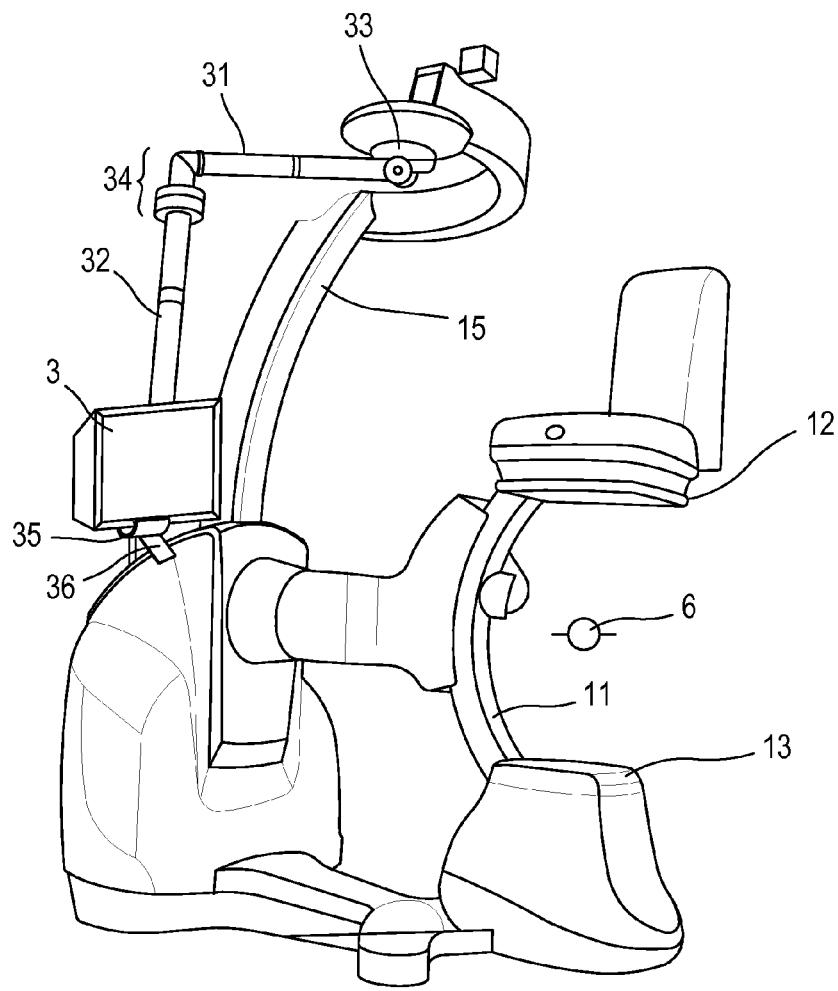
FIG. 2 illustrates an embodiment of the imaging system according to the invention.
Figure 3:
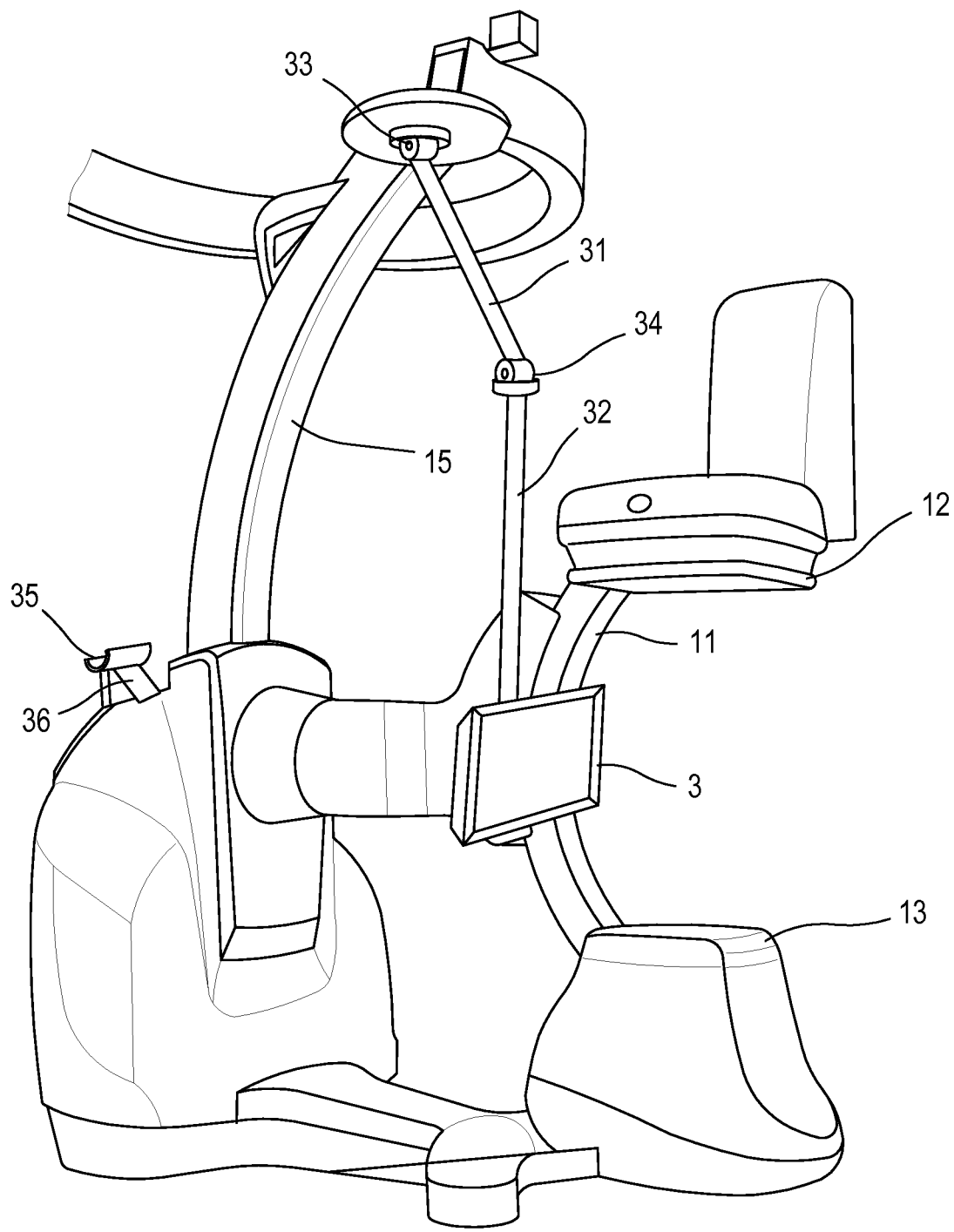
FIG. 3 illustrates an embodiment of the imaging system according to the invention.

In the embodiment illustrated in FIGS. 2 and 3, the imaging system comprises a base 35 intended to receive the display 3 when in the retracted position. The position of the base 35 is designed so that the display 3 does not form an obstacle against movement of the C-arm 11 during the acquisition of X-ray data. More generally, the presence of a base 35 defining the retracted position of the display 3 ensures that the display does not disturb the movement of the acquisition device 1 as the acquisition device 1 is capable of being moved within the operating room.

In one embodiment of the invention, the base 35 is associated with a detector 36 to detect the presence of the display 3 on the base 35. In this case, the detector is connected to a control unit controlling the movement of the C-arm. When the detector 36 detects the presence of the display 3 on the base 35, the control unit authorizes movement of the C-arm 11 for the acquisition of X-ray data. If the detector 36 does not detect the presence of the display 3 on the base 35 (i.e. the display is in deployed position) the control unit does not allow fast-speed travel of the C-arm 11.

The detector 36, for example, comprises a switch connected between a motor, allowing movement of the C-arm 11, and the power supply to the motor. When the display 3 is arranged on the base 35, the switch is in closed status which means that the motor is coupled to its power supply. In this case, the motor can move the C-arm 11 for possible acquisition of X-ray data. When the display 3 is not on the base 35, the switch is in open status which means that the motor is uncoupled from its power supply. In this case, the C-arm 11 cannot be moved.

The above-described medical imaging system allows several image-assisted surgical procedures to be performed in one operating room. The ergonomics of the medical imaging system enable each user to proceed under optimal working conditions.

The reader will appreciate that numerous modifications can be made without departing materially from the novelty and advantages described herein. For example, in the different embodiments described above, the acquisition device is a device to acquire X-ray images. However, the acquisition device may be of another type. For example the acquisition device 1 may for example be a device to acquire images by ultrasound, by magnetic resonance (MRI), by single photon emission computed tomography (SPECT), by tomodensitometry TDM or by positron emission tomography PET. Also, in the embodiment illustrated in FIGS. 2 and 3, the display is connected at the base of the acquisition device. In other embodiments, the display, for example, can be connected to the end of the C-arm comprising the sensor. The movement of the display may be manual or automatic. In this latter case, the presence of a base and/or a detector is no longer necessary, as the movements of the display may then possibly be synchronized with the movement of the C-arm or the acquisition device as a whole. Therefore any modifications of this type are intended to be incorporated within the scope of the imaging system defined in the appended claims.

What is claimed is:

1. A medical imaging system comprising:
   a movable acquisition device;
   a processing unit;
   a display, wherein the display is secured to the acquisition device via an articulated supporting structure configured to allow movement of the display between a retracted position and a deployed position; and
   a base configured to receive the display when the display is in the retracted position, the base comprising a detector configured to detect the presence of the display on the base,
   wherein the detector is operatively connected to a control unit configured to move the acquisition device when the display is on the base, and
   wherein the supporting structure comprises:
      a first telescopic arm comprising a first end and a second end, wherein each of the first end and the second end comprise an articulated connection having at least two degrees of freedom; and
      a second telescopic arm comprising a first end and a second end,
      wherein one end of the first telescopic arm is operatively connected to the acquisition device, and the other end of the first telescopic arm is operatively connected to one end of the second telescopic arm, and wherein the other end of the second telescopic arm is operatively connected to the display.

2. A medical imaging system comprising:
   a movable acquisition device;
   a processing unit;
   a display, wherein the display is secured to the acquisition device via an articulated supporting structure configured to allow movement of the display between a retracted position and a deployed position; and a base configured to receive the display when the display is in the retracted position, the base comprising a detector configured to detect the presence of the display on the base, wherein the detector is operatively connected to a control unit configured to move the acquisition device when the display is on the base, and wherein the detector comprises a switch connected to a travel unit configured to move the acquisition device, the switch having a dosed status when the display is on the base and an open status when the display is not on the base, and wherein the travel unit is inactive when the switch has open status.

3. The imaging system according to claim 2, wherein the supporting structure comprises at least one telescopic arm.

4. The imaging system according to claim 2, wherein the telescopic arm comprises a cut-out to pass connection cables, wherein the connection cables couple the display with the processing unit.

5. The imaging system according to claim 3 wherein the supporting structure comprises at least one connection having at least two degrees of freedom.

6. A medical imaging system comprising:
a movable acquisition device;
a processing unit; and
a display, wherein the display is secured to the acquisition device via an articulated supporting structure configured to allow movement of the display between a retracted position and a deployed position,
the supporting structure comprising:
a first telescopic arm comprising a first end and a second end, wherein each of the first end and the second end comprise an articulated connection having at least two degrees of freedom; and
a second telescopic arm comprising a first end and a second end,
wherein one end of the first telescopic arm is operatively connected to the acquisition device, and the other end of the first telescopic arm is operatively connected to one end of the second telescopic arm, and wherein the other end of the second telescopic arm is operatively connected to the display.

7. The imaging system according to claim 6, wherein the supporting structure comprises means to detect the position of the display relative to the acquisition device.

8. The imaging system according to claim 7, wherein the detection means comprises at least one encoder positioned in an articulation of the supporting structure.

* * * * *

UNITED STATES PATENT AND TRADEMARK OFFICE
CERTIFICATE OF CORRECTION

| | | |
|---|---|---|
| PATENT NO. | : 8,849,370 B2 | Page 1 of 1 |
| APPLICATION NO. | : 13/184195 | |
| DATED | : September 30, 2014 | |
| INVENTOR(S) | : Bouvier | |

It is certified that error appears in the above-identified patent and that said Letters Patent is hereby corrected as shown below:

In the Claims

In Column 5, Line 16, in Claim 4, delete "claim 2," and insert -- claim 3, --, therefor.

In Column 5, Line 20, in Claim 5, delete "claim 3" and insert -- claim 2, --, therefor.

Signed and Sealed this
Twenty-eighth Day of April, 2015

Michelle K. Lee
*Director of the United States Patent and Trademark Office*